(12) United States Patent
Brannan et al.

(10) Patent No.: US 9,861,439 B2
(45) Date of Patent: *Jan. 9, 2018

(54) CHOKED DIELECTRIC LOADED TIP DIPOLE MICROWAVE ANTENNA

(75) Inventors: Joseph D. Brannan, Erie, CO (US); Kyle R. Rick, Boulder, CO (US)

(73) Assignee: COVIDIEN LP, Mansfield, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/444,496

(22) Filed: Apr. 11, 2012

(65) Prior Publication Data

US 2012/0194409 A1    Aug. 2, 2012

Related U.S. Application Data

(63) Continuation of application No. 12/350,292, filed on Jan. 8, 2009, now Pat. No. 8,945,111.

(60) Provisional application No. 61/023,031, filed on Jan. 23, 2008.

(51) Int. Cl.
*A61B 18/18*     (2006.01)
*H01Q 9/16*      (2006.01)
*A61B 18/00*     (2006.01)

(52) U.S. Cl.
CPC .......... *A61B 18/1815* (2013.01); *A61B 18/18* (2013.01); *H01Q 9/16* (2013.01); *A61B 2018/00023* (2013.01); *A61B 2018/00071* (2013.01); *A61B 2018/00166* (2013.01); *A61B 2018/1838* (2013.01)

(58) Field of Classification Search
CPC ................ A61B 18/18; A61B 18/1815; A61B 2018/00023; A61B 2018/1838; A61B 2018/00005; A61B 2018/00178

USPC ........... 606/32, 33, 34, 35, 36; 607/154, 156
See application file for complete search history.

(56) References Cited

U.S. PATENT DOCUMENTS

| | | |
|---|---|---|
| 3,631,363 A | 12/1971 | Miller |
| 3,932,873 A | 1/1976 | Garcia |
| 4,140,130 A | 2/1979 | Storm, III |
| 4,375,220 A | 3/1983 | Matvias |
| 4,397,313 A | 8/1983 | Vaguine |
| 4,442,438 A | 4/1984 | Sisiak et al. |
| 4,462,412 A | 7/1984 | Turner |
| 4,572,190 A | 2/1986 | Azam et al. |
| 4,658,836 A | 4/1987 | Turner |

(Continued)

FOREIGN PATENT DOCUMENTS

| | | |
|---|---|---|
| DE | 390937 | 3/1924 |
| DE | 1099658 | 2/1961 |

(Continued)

OTHER PUBLICATIONS

US 5,326,343, 07/1994, Rudie et al. (withdrawn)

(Continued)

*Primary Examiner* — Matthew F Desanto

(57) ABSTRACT

A microwave antenna assembly is disclosed. The antenna assembly includes a feedline having an inner conductor, an outer conductor and an inner insulator disposed therebetween. A radiating portion is also included having an unbalanced dipole antenna including a proximal portion and a distal portion that are of different lengths. The proximal portion includes at least a portion of the inner conductor and the inner insulator and the distal portion includes a conductive member.

22 Claims, 9 Drawing Sheets

(56) References Cited

U.S. PATENT DOCUMENTS

| | | | |
|---|---|---|---|
| 4,662,383 A | 5/1987 | Sogawa et al. | |
| 4,798,215 A | 1/1989 | Turner | |
| 4,823,812 A | 4/1989 | Eshel et al. | |
| 5,097,844 A | 3/1992 | Turner | |
| 5,234,004 A | 8/1993 | Hascoet et al. | |
| 5,344,435 A | 9/1994 | Turner et al. | |
| 5,370,676 A | 12/1994 | Sozanski et al. | |
| 5,413,588 A | 5/1995 | Rudie et al. | |
| 5,417,210 A | 5/1995 | Funda et al. | |
| 5,417,686 A | 5/1995 | Peterson et al. | |
| 5,464,445 A | 11/1995 | Rudie et al. | |
| 5,480,417 A | 1/1996 | Hascoet et al. | |
| 5,509,929 A | 4/1996 | Hascoet et al. | |
| 5,545,137 A | 8/1996 | Rudie et al. | |
| 5,592,183 A | 1/1997 | Henf | |
| 5,599,295 A | 2/1997 | Rosen et al. | |
| 5,628,770 A | 5/1997 | Thome et al. | |
| 5,755,754 A | 5/1998 | Rudie et al. | |
| 5,776,176 A | 7/1998 | Rudie | |
| 5,800,486 A | 9/1998 | Thome et al. | |
| 5,829,519 A | 11/1998 | Uthe | |
| 5,843,144 A | 12/1998 | Rudie et al. | |
| 5,861,021 A | 1/1999 | Thome et al. | |
| 5,904,709 A | 5/1999 | Arndt et al. | |
| 5,916,240 A | 6/1999 | Rudie et al. | |
| 5,916,241 A | 6/1999 | Rudie et al. | |
| 5,931,860 A | 8/1999 | Reid et al. | |
| 5,938,692 A | 8/1999 | Rudie | |
| 5,944,749 A | 8/1999 | Fenn | |
| 5,951,546 A | 9/1999 | Lorentzen | |
| 6,007,571 A | 12/1999 | Neilson et al. | |
| 6,031,375 A | 2/2000 | Atalar et al. | |
| 6,032,078 A | 2/2000 | Rudie | |
| 6,059,780 A | 5/2000 | Gough et al. | |
| 6,097,985 A | 8/2000 | Kasevich et al. | |
| 6,134,476 A | 10/2000 | Arndt et al. | |
| 6,161,049 A | 12/2000 | Rudie et al. | |
| 6,181,970 B1 | 1/2001 | Kasevich | |
| 6,230,060 B1 | 5/2001 | Mawhinney | |
| 6,233,490 B1 | 5/2001 | Kasevich | |
| 6,275,738 B1 | 8/2001 | Kasevich et al. | |
| 6,289,249 B1 | 9/2001 | Arndt et al. | |
| 6,364,876 B1 | 4/2002 | Erb et al. | |
| 6,375,606 B1 | 4/2002 | Garibaldi et al. | |
| 6,440,158 B1 | 8/2002 | Saab | |
| 6,470,217 B1 | 10/2002 | Fenn et al. | |
| 6,485,486 B1 | 11/2002 | Trembly et al. | |
| 6,496,737 B2 | 12/2002 | Rudie et al. | |
| 6,512,956 B2 | 1/2003 | Arndt et al. | |
| 6,592,579 B2 | 7/2003 | Arndt et al. | |
| 6,603,994 B2 | 8/2003 | Wallace et al. | |
| 6,610,054 B1 | 8/2003 | Edwards et al. | |
| 6,675,050 B2 | 1/2004 | Arndt et al. | |
| 6,725,080 B2 | 4/2004 | Melkent et al. | |
| 6,725,095 B2 | 4/2004 | Fenn et al. | |
| 6,847,848 B2 | 1/2005 | Sterzer et al. | |
| 6,849,063 B1 | 2/2005 | Eshel et al. | |
| 6,866,624 B2 | 3/2005 | Chornenky et al. | |
| 6,944,504 B1 | 9/2005 | Arndt et al. | |
| 7,244,254 B2 | 7/2007 | Brace et al. | |
| 7,271,363 B2 | 9/2007 | Lee et al. | |
| 7,276,061 B2 | 10/2007 | Schaer et al. | |
| 7,311,703 B2 | 12/2007 | Turovskiy et al. | |
| 7,387,627 B2 | 6/2008 | Erb et al. | |
| 7,439,736 B2 | 10/2008 | Meaney et al. | |
| 7,467,015 B2 | 12/2008 | Van der Weide | |
| 7,565,207 B2 | 7/2009 | Turner et al. | |
| 8,945,111 B2 * | 2/2015 | Brannan | A61B 18/18 606/33 |
| 2002/0022836 A1 | 2/2002 | Goble et al. | |
| 2003/0065317 A1 | 4/2003 | Rudie et al. | |
| 2003/0100894 A1 | 5/2003 | Mahon et al. | |
| 2004/0097805 A1 | 5/2004 | Verard et al. | |
| 2004/0242992 A1 | 12/2004 | Hareyama | |
| 2005/0015081 A1 * | 1/2005 | Turovskiy et al. | 606/33 |
| 2005/0113893 A1 | 5/2005 | Saab | |
| 2005/0149010 A1 | 7/2005 | Turovskiy et al. | |
| 2005/0245920 A1 | 11/2005 | Vitullo et al. | |
| 2006/0259024 A1 | 11/2006 | Turovskiy et al. | |
| 2007/0016180 A1 | 1/2007 | Lee, Jr. et al. | |
| 2007/0016181 A1 | 1/2007 | Van Der Weide et al. | |
| 2007/0185554 A1 | 8/2007 | Appling et al. | |
| 2007/0203551 A1 | 8/2007 | Cronin et al. | |
| 2007/0233057 A1 * | 10/2007 | Konishi | 606/33 |
| 2008/0308256 A1 | 12/2008 | Deborski et al. | |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 481 685 | 4/1992 |
| EP | 0 521 264 | 1/1993 |
| EP | 0 541 930 | 5/1993 |
| EP | 0 556 705 | 8/1993 |
| EP | 0 558 429 | 9/1993 |
| EP | 0 572 131 | 12/1993 |
| EP | 0 836 868 | 4/1998 |
| EP | 1 159 926 | 5/2001 |
| EP | 1 278 007 | 1/2003 |
| EP | 1723922 A1 | 11/2006 |
| EP | 1 810 627 | 7/2007 |
| FR | 179607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| GB | 2415630 | 1/2006 |
| JP | 5-5106 | 1/1993 |
| JP | 05-40112 | 2/1993 |

(56) References Cited

FOREIGN PATENT DOCUMENTS

| | | |
|---|---|---|
| JP | 06343644 | 12/1994 |
| JP | H0714421 B2 | 2/1995 |
| JP | 07265328 | 10/1995 |
| JP | 08056955 | 3/1996 |
| JP | 08252263 | 10/1996 |
| JP | 09010223 | 1/1997 |
| JP | 2852084 B2 | 1/1999 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2002100921 A | 4/2002 |
| JP | 2005-86794 A | 3/2005 |
| JP | 2007275202 A | 10/2007 |
| SU | 166452 | 11/1964 |
| SU | 401367 | 11/1974 |
| SU | 727201 | 4/1980 |
| WO | WO96/18349 | 6/1996 |
| WO | WO97/41924 | 11/1997 |
| WO | WO97/43971 | 11/1997 |
| WO | WO97/48449 | 12/1997 |
| WO | WO97/48450 | 12/1997 |
| WO | WO97/48451 | 12/1997 |
| WO | WO00/48672 | 8/2000 |
| WO | WO00/51513 | 9/2000 |
| WO | WO00/57811 | 10/2000 |
| WO | WO01/01847 | 1/2001 |
| WO | WO01/74252 | 10/2001 |
| WO | WO02/45790 | 6/2002 |
| WO | WO02/061880 | 8/2002 |
| WO | WO03/039385 | 5/2003 |
| WO | WO2004/112628 | 12/2004 |
| WO | WO2005/011049 | 2/2005 |
| WO | WO2005/016119 | 2/2005 |
| WO | 2006002943 A1 | 1/2006 |
| WO | 2006084676 A1 | 8/2006 |
| WO | WO2007/024878 | 3/2007 |
| WO | WO2007/076924 | 7/2007 |
| WO | WO2007/112081 | 10/2007 |

OTHER PUBLICATIONS

U.S. Appl. No. 08/483,742, filed Jun. 7, 1995.
U.S. Appl. No. 08/136,098, filed Oct. 14, 1993.
U.S. Appl. No. 09/195,118, filed Nov. 18, 1998.
U.S. Appl. No. 10/244,346, filed Sep. 16, 2002.
U.S. Appl. No. 11/053,987, filed Feb. 8, 2005.
U.S. Appl. No. 12/023,606, filed Jan. 31, 2008.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/351,633, filed Jan. 9, 2009.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/401,268, filed Mar. 10, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyms PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience with the LigaSure™ Vessel Scaling System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.

(56) References Cited

OTHER PUBLICATIONS

Chou, C.K., (1995) "Radiofrequency Hyperthermia in Cancer Therapy," Chapter 94In Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Radiofrequency Lesion Generation and its Effect on Tissue Impedance", Applied Neurophysiology, 51:230-242, 1988.
Cosman et al., 'Theoretical Aspects of "Radiofrequency Lesions in the Dorsal Root Entry Zone" Neurosurgery 15:(1984), pp. 945-950.
Cosman et al., "Methods of Making Nervous System Lesions" In William RH, Rengachary SS (eds): Neurosurgery, New York: McGraw-Hill, vol. III, (1984), pp. 2490-2499.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline Product Literature, "Light Key: Visualize a Virtual Keyboard. One with No Moving Parts", 4 pages.
Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part 1", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Johnson et al., "Evaluation of a Bipolar Electrothermal Vessel Sealing Device in Hemorrhoidectomy" Sales/Product Literature, Jan. 2004.
Jarrett et al., "Use of the LigaSure™ Vessel Sealing System for Peri-Hilar Vessels in Laparoscopic Nephrectomy" Sales/Product Literature 2000.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Mar. 2000) I'D Wire: product description, 1 page.
MDTECH product literature (Dec. 1999) "FlexStrand": product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences-Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. 1, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.

(56) References Cited

OTHER PUBLICATIONS

Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
S. Humphries Jr. et al., "Finite-Element Codes to Model Electrical Heating and Non-Linear Thermal Transport in Biological Media", Proc. ASME HTD-355, 131 (1997).
Urologix, Inc.-Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Esterline Product Literature, "Light Key: Visualize a Virtual Keyboard. One With No Moving Parts", Nov. 1, 2003; 4 pages.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.

(56) References Cited

OTHER PUBLICATIONS

European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.
Extended European Search Report from Appl. No. EP 09704429.1 dated Mar. 23, 2011.
Chinese Office Action, Application No. 200980103070.7 dated Jun. 9, 2015.
Extended European Search Report from Appl. No. 15201968.3 dated May 2, 2016.
ESR14154455.1 European Search Report dated Apr. 30, 2014.
Extended European Search Report corresponding to European Application No. EP 14 153 419.8, dated Apr. 15, 2014; 6 pages.
Japanese Office Action and English language translation issued in Appl. No. JP 2010-5411104 dated Jun. 27, 2013.
Australian Examination Report issued in Appl. No. AU 2009206445 dated Nov. 29, 2012.

\* cited by examiner

CHOKED DIELECTRIC LOADED TIP DIPOLE MICROWAVE ANTENNA

CROSS-REFERENCE TO RELATED APPLICATIONS

This application claims the benefit of priority to U.S. Provisional Application Ser. No. 61/023,031 entitled "CHOKED DIELECTRIC LOADED TIP DIPOLE MICROWAVE ANTENNA" filed Jan. 23, 2008 by Joseph D. Brannan, and is a Continuation of U.S. patent application Ser. No. 12/350,292 entitled "CHOKED DIELECTRIC LOADED TIP DIPOLE MICROWAVE ANTENNA" filed Jan. 8, 2009 by Joseph D. Brannan and Kyle R. Rick, both of which are incorporated by reference herein.

BACKGROUND

1. Technical Field

The present disclosure relates generally to microwave applicators used in tissue ablation procedures. More particularly, the present disclosure is directed to a microwave applicator having either a liquid or solid loaded tip dipole antenna.

2. Background of Related Art

Treatment of certain diseases requires destruction of malignant tissue growths (e.g., tumors). It is known that tumor cells denature at elevated temperatures that are slightly lower than temperatures injurious to surrounding healthy cells. Therefore, known treatment methods, such as hyperthermia therapy, heat tumor cells to temperatures above 41° C., while maintaining adjacent healthy cells at lower temperatures to avoid irreversible cell damage. Such methods involve applying electromagnetic radiation to heat tissue and include ablation and coagulation of tissue. In particular, microwave energy is used to coagulate and/or ablate tissue to denature or kill the cancerous cells.

Microwave energy is applied via microwave ablation antennas that penetrate tissue to reach tumors. There are several types of microwave antennas, such as monopole and dipole. In monopole and dipole antennas, microwave energy radiates perpendicularly from the axis of the conductor. A monopole antenna includes a single, elongated microwave conductor. Dipole antennas may have a coaxial construction including an inner conductor and an outer conductor separated by a dielectric portion. More specifically, dipole microwave antennas may have a long, thin inner conductor that extends along a longitudinal axis of the antenna and is surrounded by an outer conductor. In certain variations, a portion or portions of the outer conductor may be selectively removed to provide for more effective outward radiation of energy. This type of microwave antenna construction is typically referred to as a "leaky waveguide" or "leaky coaxial" antenna.

Conventional microwave antennas have a narrow operational bandwidth, a wavelength range at which optimal operational efficiency is achieved, and hence, are incapable of maintaining a predetermined impedance match between the microwave delivery system (e.g., generator, cable, etc.) and the tissue surrounding the microwave antenna. More specifically, as microwave energy is applied to tissue, the dielectric constant of the tissue immediately surrounding the microwave antenna decreases as the tissue is cooked. The drop causes the wavelength of the microwave energy being applied to tissue to increase beyond the bandwidth of the antenna. As a result, there is a mismatch between the bandwidth of conventional microwave antenna and the microwave energy being applied. Thus, narrow band microwave antennas may detune hindering effective energy delivery and dispersion.

SUMMARY

According to one aspect of the present disclosure a microwave antenna assembly is disclosed. The antenna assembly includes an unbalanced dipole antenna, a shorted choke having a dielectric layer extending past the conductor layer and connection hub coupled to a coolant system for circulating a dielectric coolant fluid through the antenna assembly.

According to another aspect of the present disclosure a microwave antenna assembly is disclosed. The antenna assembly includes a feedline having an inner conductor, an outer conductor and an inner insulator disposed therebetween. A radiating portion is included which has an unbalanced dipole antenna having a proximal portion and a distal portion that is longer than the proximal portion. The proximal portion includes at least a portion of the inner conductor and the inner insulator and the distal portion includes a conductive member. The antenna assembly also includes a choke disposed around at least a portion of the feedline. The choke includes an inner dielectric layer and an outer conductive layer, wherein the outer conductive layer is shorted to the outer conductor of the feedline and the inner dielectric layer extends past the outer conductive layer. The assembly further includes a sheath disposed over the feedline and the radiating portion, the sheath defines a chamber around the feedline and the radiating portion, the chamber being adapted to circulate dielectric coolant fluid therethrough.

According to a further aspect of the present disclosure a microwave antenna assembly is disclosed. The antenna assembly includes a feedline having an inner conductor, an outer conductor and an inner insulator disposed therebetween and a radiating portion including an unbalanced dipole antenna having a proximal portion and a distal portion that are of different lengths. The proximal portion includes at least a portion of the inner conductor and the inner insulator and the distal portion includes a conductive member. The antenna assembly also includes a choke disposed around at least a portion of the feedline. The choke includes an inner dielectric layer and an outer conductive layer, wherein the outer conductive layer is shorted to the outer conductor of the feedline and the inner dielectric layer extends past the outer conductive layer. The antenna assembly further includes a coolant jacket disposed over the feedline defining a proximal chamber around the feedline, the chamber being adapted to circulate dielectric coolant fluid therethrough and a solid dielectric loading having central cavity defined therein adapted to fit about the radiating portion, the solid dielectric loading extending from the coolant jacket.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure will be described herein below with reference to the accompanying drawings. In the following description, well-known functions or constructions are not described in detail to avoid obscuring the present disclosure in unnecessary detail.

Figure 1:
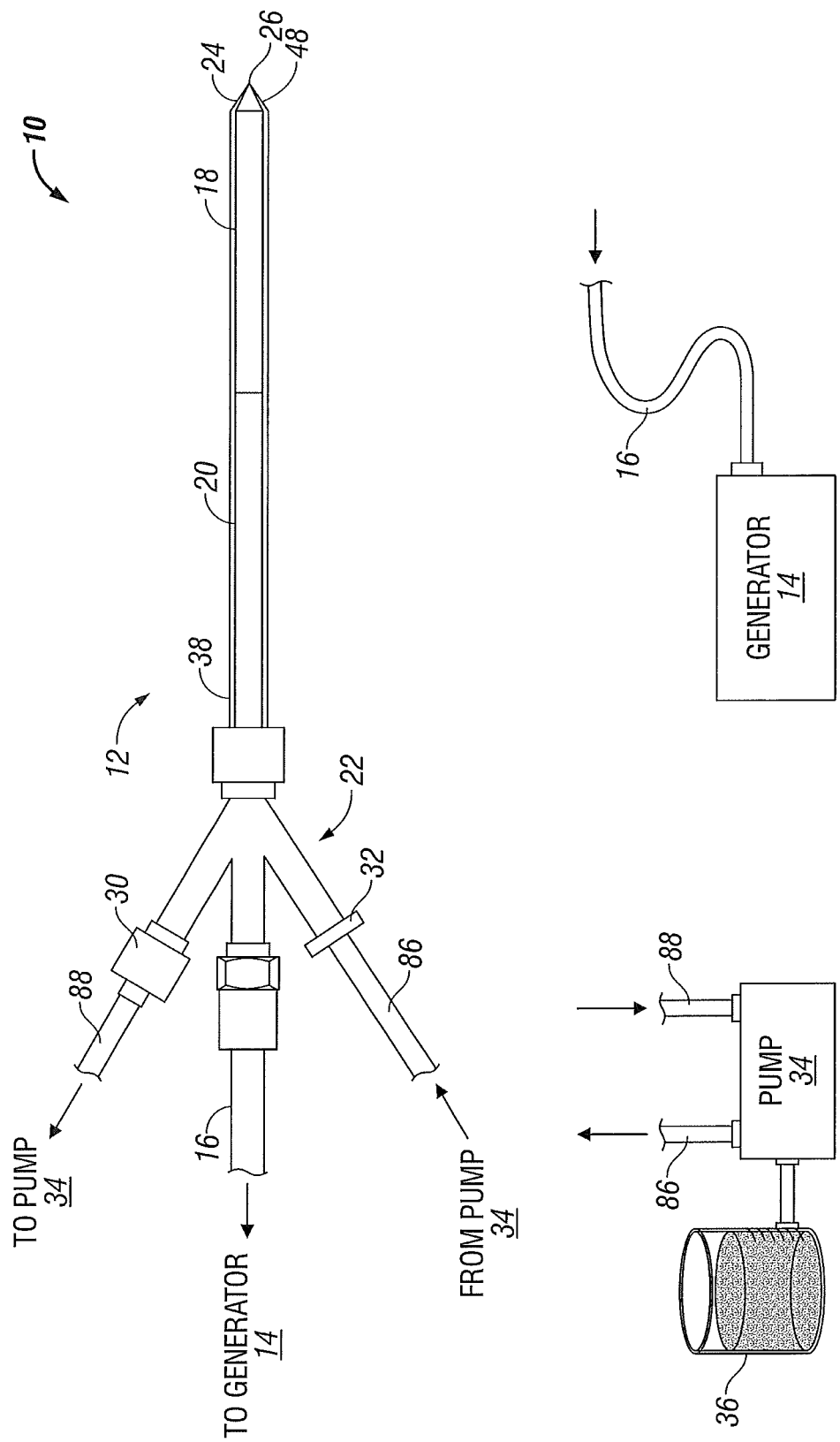
FIG. 1 is a schematic diagram of a microwave ablation system according to an embodiment of the present disclosure.

FIG. 1 shows a microwave ablation system 10 that includes a microwave antenna assembly 12 coupled to a microwave generator 14 via a flexible coaxial cable 16. The generator 14 is configured to provide microwave energy at an operational frequency from about 500 MHz to about 5000 MHz.

The antenna assembly 12 is generally comprised of radiating portion 18, which may be connected by feedline 20 (or shaft) to the cable 16. More specifically, the antenna assembly 12 is coupled to the cable 16 through a connection hub 22. The connection hub 22 also includes an outlet fluid port 30 and an inlet fluid port 32 that are connected in fluid communication with a sheath 38. The sheath 38 encloses the radiating portion 18 and the feedline 20 allowing for coolant fluid from the ports 30 and 32 to be supplied and circulated around the antenna assembly 12. The ports 30 and 32 are also coupled to a supply pump 34 that is, in turn, coupled to a supply tank 36. The supply tank 36 stores the coolant fluid and maintains the fluid at a predetermined temperature. In one embodiment, the supply tank 36 may include a coolant unit which cools the returning liquid from the antenna assembly 12. In another embodiment, the coolant fluid may be a gas and/or a mixture of fluid and gas.

Assembly 12 also includes a tip 48 having a tapered end 24 that terminates, in one embodiment, at a pointed end 26 to allow for insertion into tissue with minimal resistance at a distal end of the radiating portion 18. In those cases where the radiating portion 18 is inserted into a pre-existing opening, tip 48 may be rounded or flat.

Figure 2:
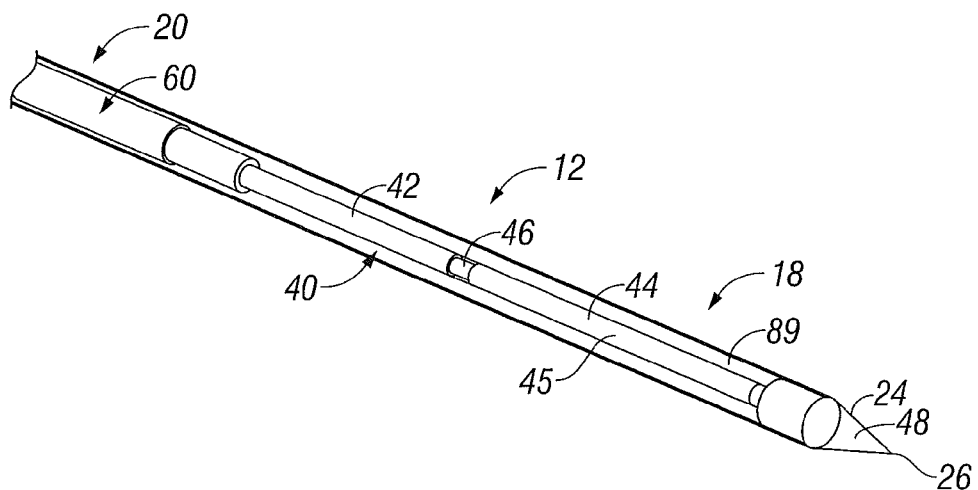
FIG. 2 is a perspective cross-sectional view of a microwave antenna assembly according to the present disclosure.
Figure 3:
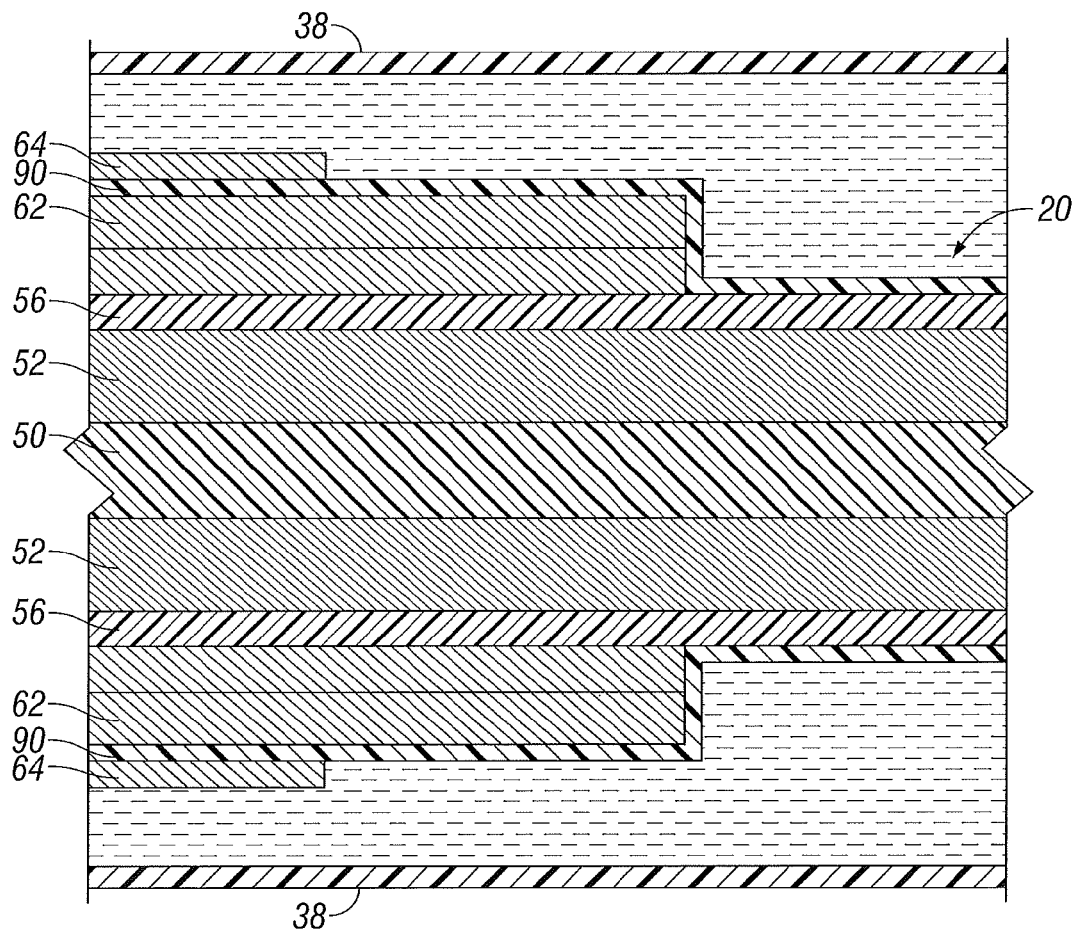
FIG. 3 is an enlarged cross-sectional of a portion of the microwave antenna assembly of FIG. 2.
Figure 4:
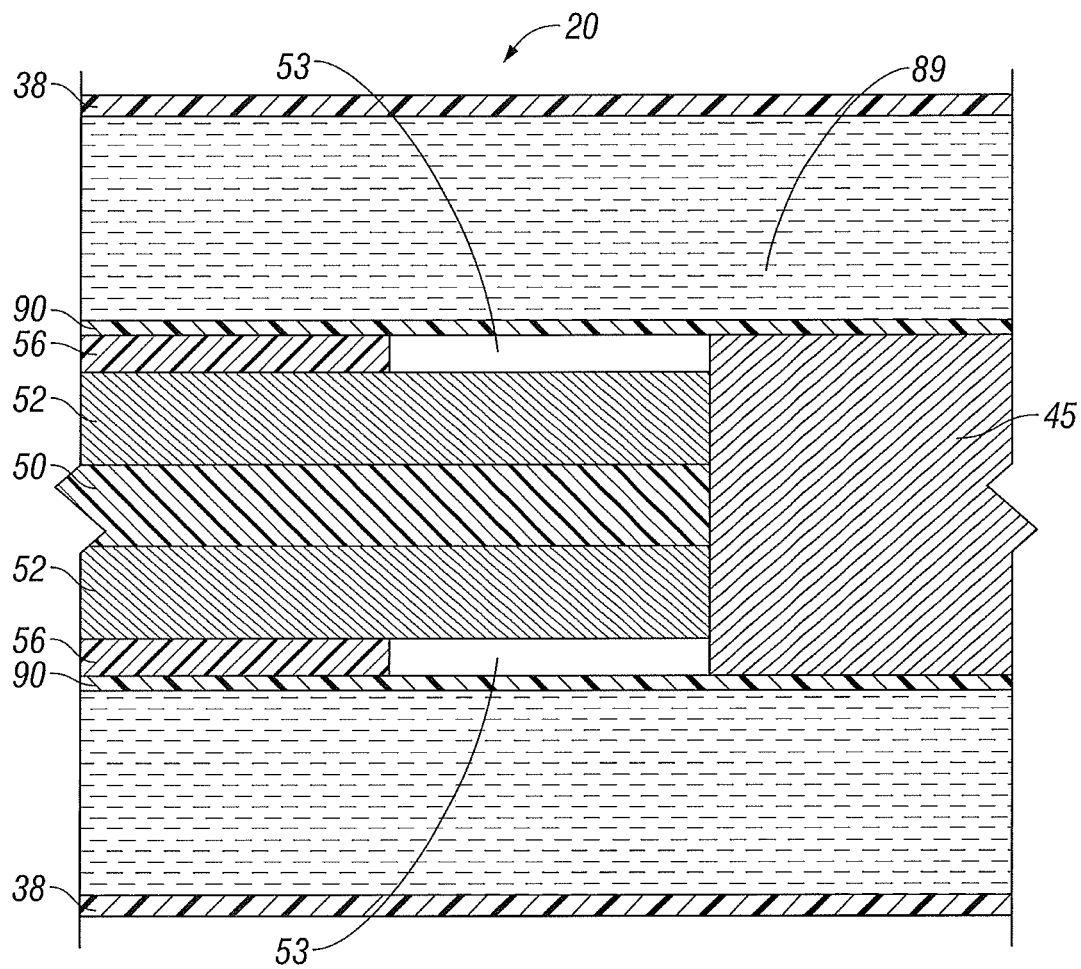
FIG. 4 is an enlarged cross-sectional of a portion of the microwave antenna assembly of FIG. 2.

FIG. 2 illustrates the radiating portion 18 of the antenna assembly 12 having an unbalanced dipole antenna 40. The dipole antenna 40 is coupled to the feedline 20 that electrically connects antenna assembly 12 to the generator 14. As shown in FIG. 3-4, the feedline 20 includes an inner conductor 50 (e.g., wire) surrounded by an inner insulator 52, which is then surrounded by an outer conductor 56 (e.g., cylindrical conducting sheath). The inner and outer conductors may be constructed of copper, gold, stainless steel or other conductive metals with similar conductivity values. The metals may be plated with other materials, e.g., other conductive materials, to improve their properties, e.g., to improve conductivity or decrease energy loss, etc. In one embodiment, the feedline 20 may be formed from a coaxial semi-rigid or flexible cable having a wire with a 0.047" outer diameter rated for 50 Ohms.

Figure 5:
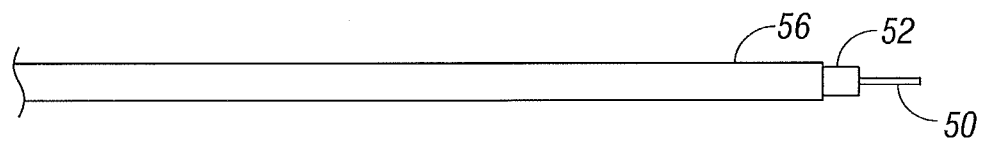
FIG. 5 is a side view of a distal portion of a feedline of the microwave antenna assembly of FIG. 2.
Figure 7:
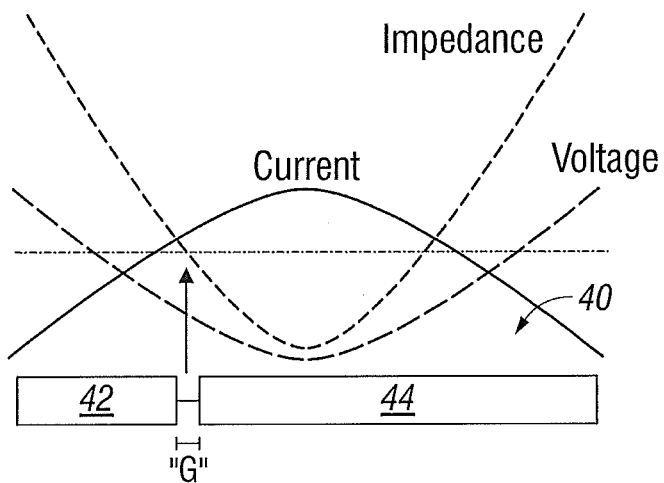
FIG. 7 is a schematic illustration of an unbalanced dipole antenna according to an embodiment of the present disclosure.

The dipole antenna 40 includes a proximal portion 42 and a distal portion 44 interconnected by a dielectric spacer at a feed point 46. The distal portion 44 and the proximal portion 42 are of different, unequal lengths so that the dipole antenna 40 is unbalanced. In one embodiment, as shown in FIG. 7, the distal portion 44 may be longer than the proximal portion 42. The proximal portion 42 is formed from the inner conductor 50 and the inner insulator 52 which are extended outside the outer conductor 56, as shown best in FIG. 4. In one embodiment, in which the feedline 20 is formed from a coaxial cable, the outer conductor 56 and the inner insulator 52 may be sliced off to reveal the inner conductor 50, as shown in FIG. 5.

The distal portion 44 includes a conductive member 45 that may be formed from any type of conductive material, such as metals (e.g., copper, stainless steel, tin, and various alloys thereof). The distal portion 44 may have a solid structure and may be formed from solid wire (e.g., 10 AWG). In another embodiment, the distal portion 44 may be formed from a hollow sleeve of an outer conductor of coaxial cable or another cylindrical conductor. The cylindrical conductor may then be filled with solder to convert the cylinder into a solid shaft. More specifically, the solder may be heated to a temperature sufficient to liquefy the solder within the cylindrical conductor (e.g., 500° F.) thereby creating a solid shaft.

In another embodiment, the conductive member 45 may also be formed from solid wire or a cylindrical conductor filled with solder. The conductive member 45 is thereafter coupled to the inner conductor 50, as shown in FIG. 4. This may be accomplished by soldering the conductive member 45 to the distal end of the inner conductor 50, such as by melting the solder of the conductive member 45 and inserting the inner conductor 50 therein.

Figure 6:
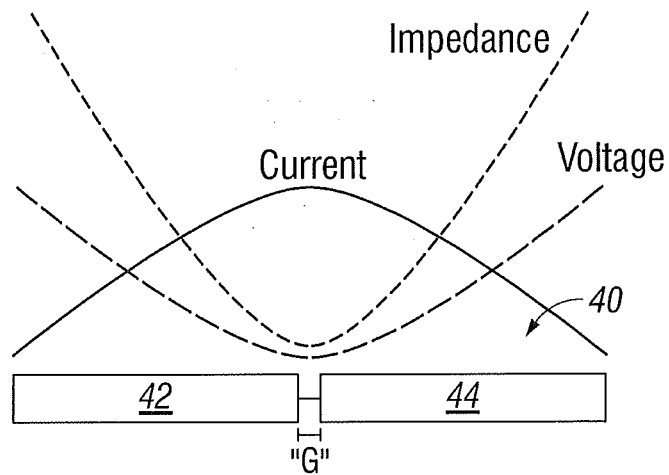
FIG. 6 is a schematic illustration of a balanced dipole antenna according to an embodiment of the present disclosure.

In some embodiments, the unbalanced dipole antenna 40 provides for better impedance matching during ablation. Variation in tissue properties during ablation complicates real part impedance matching of microwave ablation antennas. Over the course of an ablation, a given position on the dipole varies in real impedance due to the resulting dynamic current and voltage relationship. FIG. 6 shows the difficulty in matching real part impedance using a half-wave dipole antenna which includes two portions of equal lengths, at the center of the dipole the voltage is minimized and the current is maximized. However, the real part impedance is minimized and is maximized at the ends of the proximal and distal portions 42 and 44. In contrast, the unbalanced dipole antenna 40 of the present disclosure minimizes the integration over ablation time of the difference between the feed point real part impedance and the impedance of the cable 16. As illustrated in FIG. 7, the unbalanced half-wave dipole provides a better match of initial impedance to real part impedance by placing the gap between the proximal and distal portions 42 and 44 away from the center of the dipole antenna 40. In one embodiment, the length of the distal portion 40 is about 40 mm to minimize return loss of the assembly 12.

Figure 8:
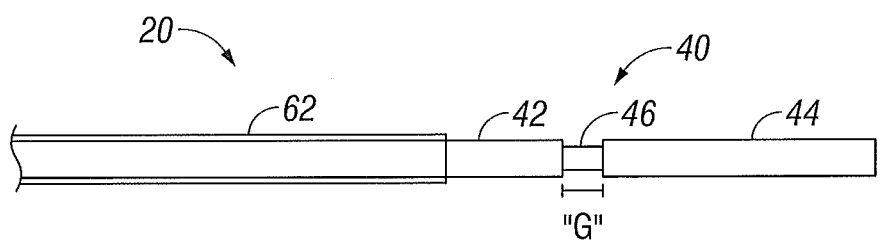
FIG. 8 is a side view of the unbalanced dipole antenna of the microwave antenna assembly of FIG. 2.

FIG. 8 illustrates the distal portion 44 attached to the proximal portion 42. The distal portion 44 may be soldered to the inner conductor 50 of the proximal portion 42 to establish electromechanical contact therebetween. In one embodiment, where the distal portion 44 is formed from a hollow cylindrical conductor filled with a solder material, the distal portion 44 may be attached to the proximal portion 42 by liquefying the solder of the distal portion 44 and inserting the distal end of the inner conductor 50 therein. A portion of the distal end of the inner conductor 50 is inserted into the distal portion 44 such that a dipole feed gap "G" remains between the proximal and distal portions 42 and 44 at the feed point 46. The gap "G" may be from about 1 mm to about 3 mm. The dipole feed gap of the antenna is the first structure the coaxial field mode encounters upon transfer to free space. The gap therefore plays an important role in the return loss, or system-to-antenna impedance match. In one embodiment, the gap "G" is thereafter filled with a dielectric material to form the dielectric spacer at the feed point 46. In another embodiment, the inner insulator 52 is extended into the feed point 46. The dielectric material may be polytetrafluoroethylene (PTFE), such as Teflon® sold by DuPont of Willmington, Del. In another embodiment, as shown in FIG. 4, the gap "G" may be coated via a dielectric seal coating as discussed in more detail below.

Figure 9:
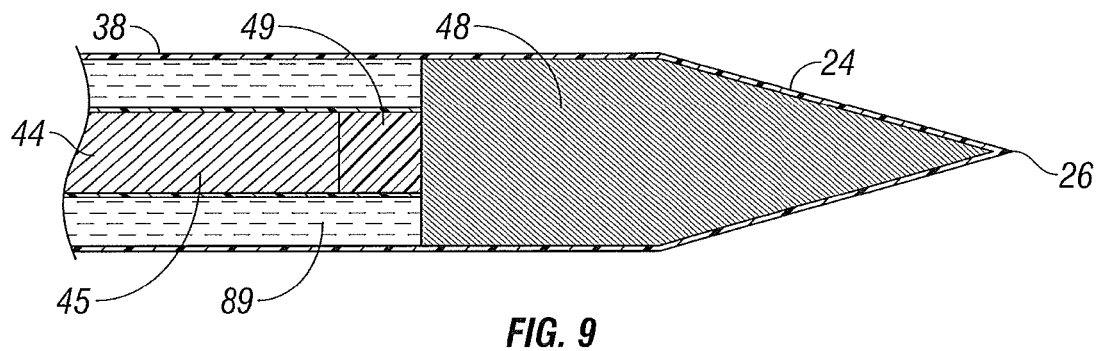
FIG. 9 is an enlarged cross-sectional of a distal end of the microwave antenna assembly of FIG. 2.

As shown in FIGS. 2 and 9, the distal portion 44 is coupled to the tip 48, which may be formed from a variety of heat-resistant materials suitable for penetrating tissue, such as metals (e.g., stainless steel) and various thermoplastic materials, such as poletherimide, polyamide thermoplastic resins, an example of which is Ultem® sold by General Electric Co. of Fairfield, Conn. The tip 48 may be machined from various stock rods to obtain a desired shape. The tip 48 may be attached to the distal portion 44 using various adhesives, such as epoxy seal 49. If the tip 48 is metal, the tip 48 may be soldered to the distal portion 44.

Figure 11:
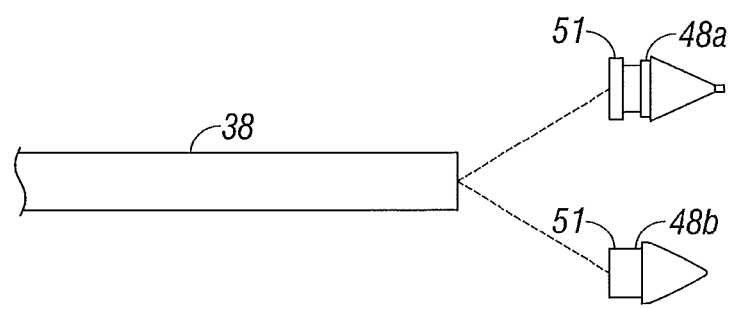
FIG. 11 is a side view of a tip and a sheath of the microwave antenna assembly of FIG. 2.

FIG. 11 illustrates various shapes and forms of the tip 48, namely a stainless steel tip 48a and a dielectric tip 48b. Both tips 48a and 48b includes an insertion base 51 having an external diameter that is smaller than diameter of the tips 48a and 48b allowing for easier insertion into the sheath 38. This configuration also provides for a better seal between the tip 48 and the sheath 38 as discussed in more detail below.

With reference to FIGS. 2 and 3, the antenna assembly 12 also includes a choke 60. The choke 60 is disposed around the feedline 20 and includes an inner dielectric layer 62 and an outer conductive layer 64. In one embodiment, the choke 60 is a proximally positioned quarter-wave length shorted choke. The choke 60 is implemented as a quarter-wave length shorted by using the outer conductive layer 64 around the outer conductor 56 of the feedline 20 separated by the dielectric layer. The choke 60 is shorted to the outer conductor 56 of the feedline 20 at the proximal end of the choke 60 by soldering or other means. In one embodiment, the dielectric layer 62 is formed from a fluoropolymer, such as tetrafluorethylene, perfluorpropylene, and the like, and has a thickness of 0.005 inches. The outer conductive layer 64 may be formed from a so-called "perfect conductor" material, such as a highly conductive metal (e.g., copper).

In embodiments, the choke 60 may be a quarter-wavelength shorted choke, a half-wavelength open choke, and inverted quarter-wavelength shorted choke or a gap cancellation choke. The choke 60 confines the microwave energy from the generator 14 to the radiating portion 18 of the assembly 12, thereby limiting the microwave energy deposition zone length along the feedline 20. The choke 60 provides high impedance to microwave energy conducted down the outside of the feedline 20, thereby limiting energy deposition to the end of the antenna.

A shorted quarter-wave choke placed at the high impedance point of the proximal portion 42 on the antenna assembly 12 confines antenna currents to the radiating section 18 of the assembly 12, reducing the length and maximizing the cross sectional diameter of ablations due to nearly spherical power dissipation zones.

Figure 10:
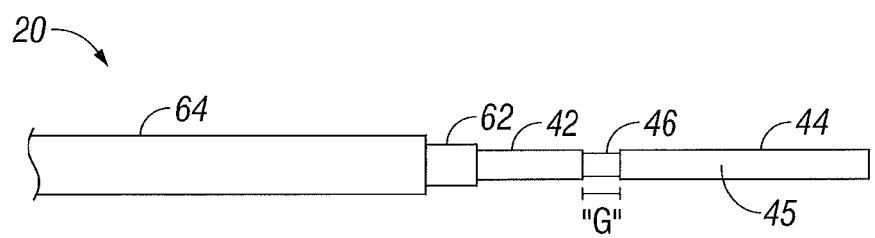
FIG. 10 is a side view of a radiating portion of the microwave antenna assembly of FIG. 2.

The dielectric of dielectric layer 62 extends past the choke conductor layer 64 toward the distal end of the assembly 12, as shown in FIG. 10. In one embodiment, the dielectric layer 62 may extend past the choke conductor layer 64 by about 6 mm. This extended dielectric improves the performance of the choke 60 by placing a capacitance between the proximal portion 42 of the dipole and the outer surface of the choke conductor layer 64 thereby blocking currents from jumping onto the choke conductor layer 64. The capacitance formed by the dielectric is a high impedance barrier to microwave currents which would otherwise jump from the proximal portion 42 to the outer surface of the choke 60 near the entrance thereof, avoiding the choke structure completely. Instead, these currents are directed into the quarter-wave choke 60 by the capacitance, improving its effectiveness.

As discussed above, the wavelength increase due to tissue desiccation causes the high impedance point on the proximal portion 42 to move proximally along the assembly 12. An effective choke must present high impedance at this variable point. The extended dielectric effectively acts as a variable position choke, covering the range over which this point shifts, maintaining choke effectiveness as long as the high impedance point of the proximal portion 42 stays within the extended dielectric boundaries. The dielectric layer 62 may be extended to any length between the choke conductive layer 64 and the feed point 46.

In one embodiment, the dielectric layer 62 may be formed by applying a dielectric shrink material, such as 5/64" thick PTFE shrink wrap to the outer conductor 56. Once the shrink wrap material is placed around the outer conductor 56, the material is heated so that the material melts and sets about the outer conductor 56. The heating may be accomplished by hot air blowers, which can provide a hot air stream of about 750° F. Multiple layers of the PTFE shrink wrap may be applied and consecutively heated to form the dielectric layer 62 of desired thickness. In one embodiment, three or more layers of the PTFE shrink wrap are applied.

Figure 12:
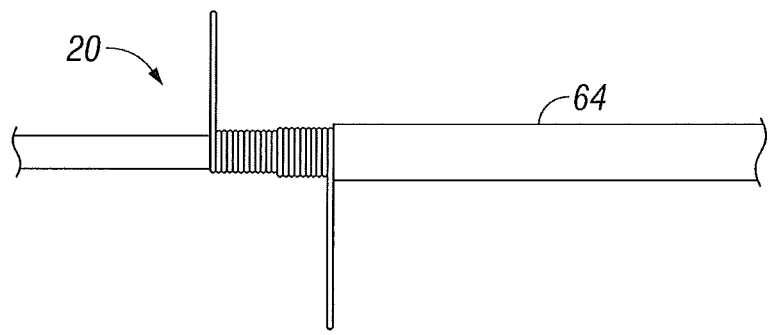
FIG. 12 is a side view of is proximal end of the feedline of the microwave antenna assembly of FIG. 2.

As shown in FIGS. 3 and 10, the conductor layer 64 may be formed by applying one or more layers of a conductive metal foil (e.g., copper) onto the dielectric layer 62. The foil may extend past the proximal end of the dielectric layer 62 as shown in FIG. 12. The foil may be attached to the dielectric layer 62 using various types of adhesives (e.g., ultraviolet light activated glue, epoxy, etc.). In one embodiment, the proximal end of the foil which extends past the dielectric layer 62 may be attached to the feedline 20 by means of a so-called "wire-wrap" technique to provide a good electrical connection to the foil and the feedline 20 as shown in FIG. 12. The wire is wrapped around the copper foil at the point where the foil begins to taper down past the dielectric layer 62. After the wire is wrapped, the wire is soldered to itself all along the length of the wrap to secure the wire and prevent the wire from unwrapping. In another embodiment, other means may be used to secure the foil to the feedline 20, such as a hollow cylinder may be placed around the excess foil necking down past the dielectric layer 62. In a further embodiment, the foil may be substantially the same length as the dielectric layer 62 to obviate the need for securing the proximal end of the foil to the feedline 20.

Figure 13:
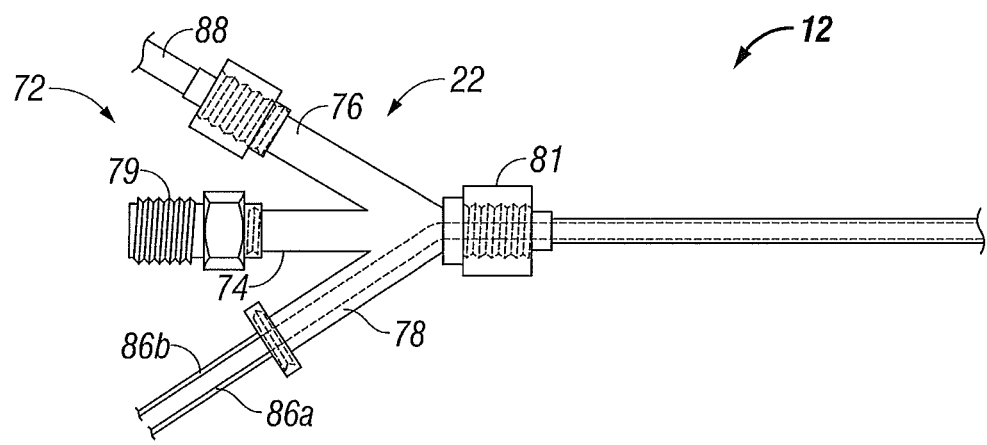
FIG. 13 is a cross-sectional view of the connection hub and a proximal end f the microwave antenna assembly of FIG. 2.

The assembly 12 also includes the connection hub 22 of FIG. 1, as shown in more detail in FIG. 13. The connection hub 22 includes a cable connector 79 and fluid ports 30 and 32. The connection hub 22 may include a three-branch luer type connector 72, with a middle finger 74 being used to house the cable connector 70 and the left and right fingers 76 and 78 to house the outlet and inlet fluid ports 30 and 32, respectively. The connection hub 22 also includes a base 81 disposed at a distal end of the middle finger 74.

Figure 14:
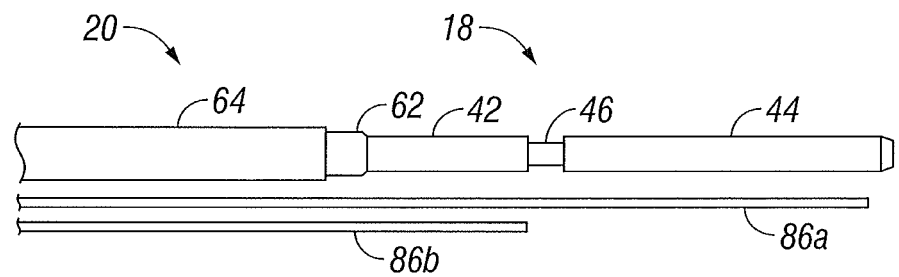
FIG. 14 is a schematic view of inflow tubes of the microwave antenna assembly of FIG. 2.

The assembly 12 also includes an active coolant system as shown in FIGS. 1, 13 and 14. More specifically, the assembly 12 includes sheath 38 that encloses the feedline 20, the radiating portion 18 from the tip 48 to the base 81. The coolant is supplied by the pump 34 and is circulated in the space between the radiating portion 18, the feedline 20 and the sheath 38. Since the radiating portion 18 and the feedline 20 are in direct contact with the coolant fluid these components of the assembly 12 should be sealed to prevent any fluid seeping therein. This may be accomplished by applying any type of melt-processible polymers using conventional injection molding and screw extrusion techniques. In one embodiment, a sleeve 90 of fluorinated ethylene propylene (FEP) shrink wrap as shown in FIGS. 3 and 4 may be applied to the entire assembly 12, namely the feedline 20 and the radiating portion 18, as shown in FIG. 1. The FEP sleeve 90 is then heated to seal the feedline 20 and radiating portion 18. The resulting FEP seal prevents any coolant fluid from penetrating into the assembly 12. The FEP sleeve 90 may be applied either prior to (FIG. 3) or after applying the outer conductive layer 64. In addition, FEP may also be applied at the point where the inner conductor 50 and the inner insulator 52 are extended past the outer conductor 56, thereby creating a vacuum 53 as shown in FIG. 4.

The sheath 38 may be any type of rigid tube, such as a catheter manufactured from polyimide and other types of polymers. The sheath 38 may be assembled by initially securing the tip 48 to the distal end of the sheath 38 and then inserting the combined sheath and tip assembly onto the assembly 12. The sheath 38 is also secured to the base 81 of the connection hub 22 and the tip 48 such that the sheath 38 is in fluid communication with the connection hub 22 and defines a chamber 89 between the base 81 and the tip 48.

The inflow tube 86 may include one or more inflow tubes 86a and 86b. The inflow tubes 86a and 86b may be any type of flexible tube having an external diameter sufficient to fit inside the chamber 89 (FIGS. 4 and 9) between the feedline 20 and the sheath 38. The inflow tubes 86a and 86b are inserted through the outlet fluid port 30. More specifically, the inflow tube 86a is inserted almost to the distal end of the distal portion 44 and the inflow tube 86b is inserted approximately to the feed point 46 as shown in FIG. 14. The inflow tubes 86a and 86b are then secured to the radiating portion 18 (e.g., using epoxy, glue, etc.). The inflow tubes 86a and 86b are positioned in this configuration to provide for optimal coolant flow through the sheath 38. The fluid flow from the inflow tube 86a is ejected into the tip 48 and is reflected in the proximal direction. The fluid flow from the inflow tube 86b provides for the coolant along the radiating portion 18. During operation, the pump 34 supplies fluid to the assembly 12 through the inflow tubes 86a and 86b, thereby circulating the coolant through the entire length of the assembly 12 including the connection hub 22. The fluid is then withdrawn from the middle finger 74 and the left finger 76 through the outlet fluid port 32.

The above-discussed coolant system provides for circulation of dielectric coolant fluid (e.g., saline, deionized water, etc.) through the entire length of the antenna assembly 12. The dielectric coolant fluid removes the heat generated by the assembly 12. In addition, the dielectric coolant fluid acts as a buffer for the assembly 12 and prevents near field dielectric properties of the assembly 12 from changing due varying tissue dielectric properties. As microwave energy is applied during ablation, desiccation of the tissue around the radiating portion 18 results in a drop in tissue complex permittivity by a considerable factor (e.g., about 10). The dielectric constant (er') drop increases the wavelength of microwave energy in the tissue, which dramatically affects the impedance of un-buffered microwave antenna assemblies, thereby mismatching the antenna assemblies from the system impedance (e.g., impedance of the cable 16 and the generator 14). The increase in wavelength also results in a power dissipation zone which is much longer in length along the assembly 12 than in cross sectional diameter. The decrease in tissue conductivity (er") also affects the real part of the impedance of the assembly 12. The fluid dielectric buffering according to the present disclosure also moderates the increase in wavelength of the delivered energy and drop in conductivity of the near field, thereby reducing the change in impedance of the assembly 12, allowing for more consistent antenna-to-system impedance match and spherical power dissipation zone despite tissue behavior.

The buffering of wavelength variation also allows for a more effective choking network. The choke must be placed at the low current point, or high impedance point, on the end of the proximal portion 42. With wavelength buffering in the choked wet tip, the half wavelength current pattern on the dipole radiating section is maintained, making the position of the high impedance point less variable and therefore allowing for a more effective choke network. Together, the cable cooling and the dielectric buffering allow for targeted and efficient energy delivery to the tissue to enable nearly spherical ablation zones and fast ablation times. Either saline or deionized water can be used with the assembly 12.

FIGS. 15-18 illustrate another embodiment of a microwave antenna assembly 112 of having a radiating portion 118 and a feedline 120 which couples the assembly 112 to the cable 16. More specifically, the antenna assembly 112 is coupled to the cable 16 through a connection hub 122 that includes an outlet fluid port 130 and an inlet fluid port 132.

Figure 16:
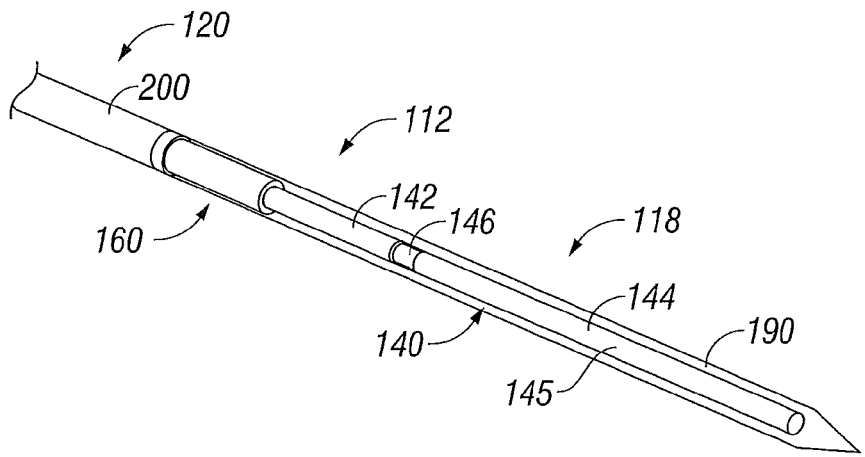
FIGS. 16 and 17 are perspective cross-sectional views of the microwave antenna of FIG. 15.
Figure 17:
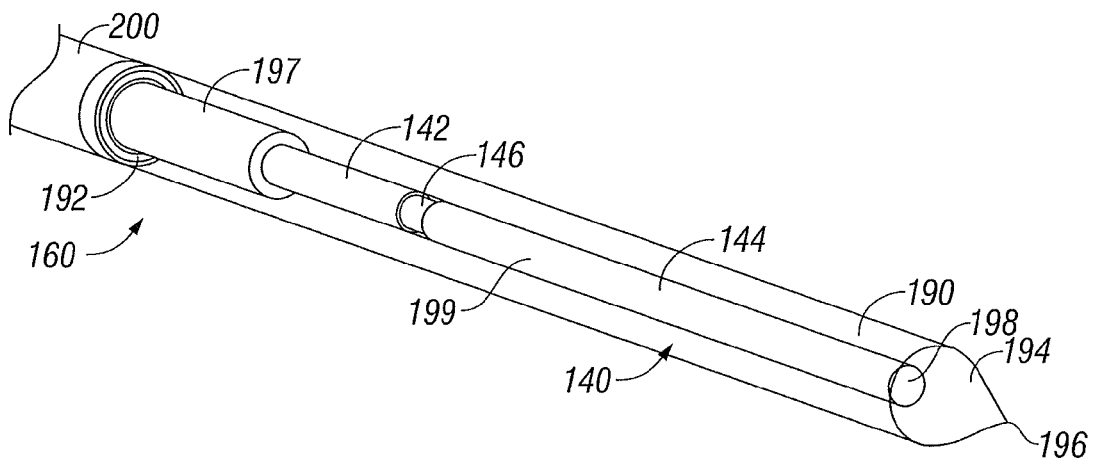
Figure 18:
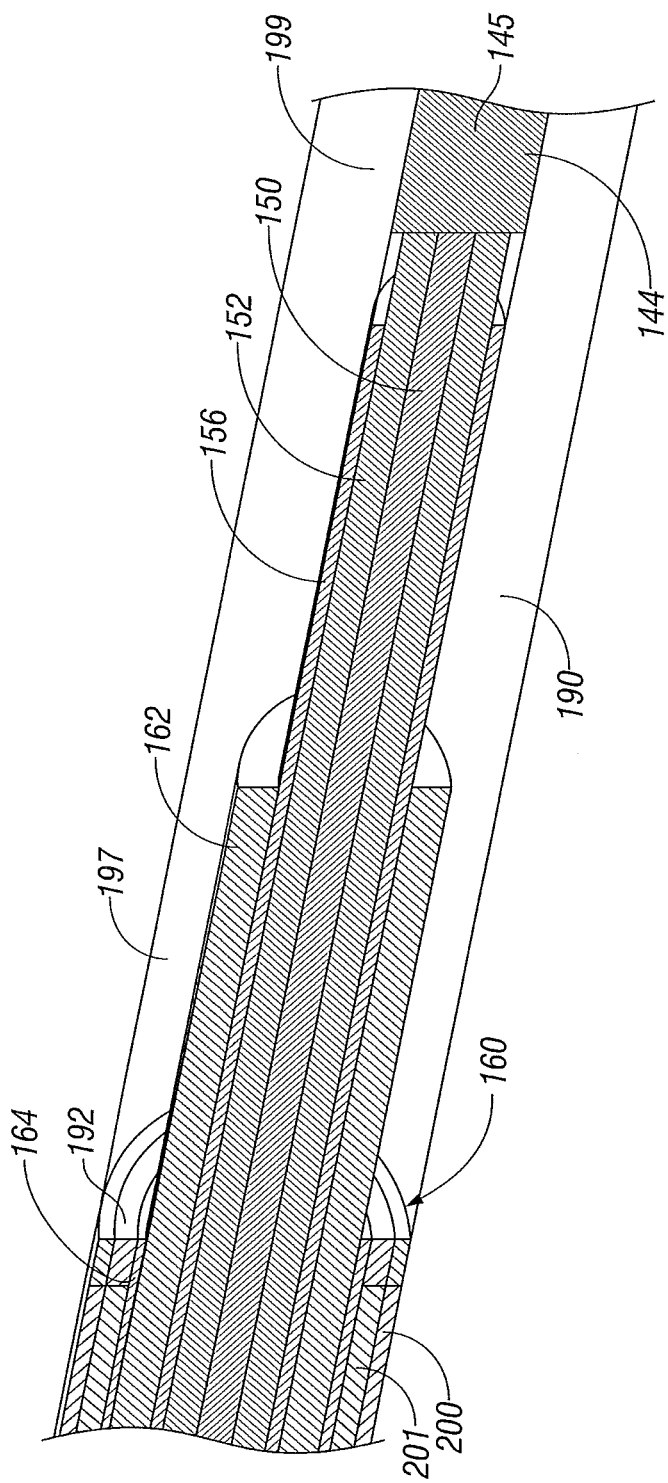
FIG. 18 is a cross-sectional enlarged perspective view of the microwave antenna of FIG. 15.

FIGS. 16 and 17 illustrate the radiating portion 118 of the antenna assembly 112 having an unbalanced dipole antenna 140 in which the sheath 38 is replaced by a metallic conduit (e.g., coolant jacket 200) and a solid dielectric loading 190. The dipole antenna 140 is coupled to the feedline 120, which electrically connects antenna assembly 112 to the generator 14. As shown in FIG. 18, similar to the feedline 20, the feedline 120 includes an inner conductor 150 (e.g., wire) surrounded by an inner 152 insulator which is then surrounded by an outer conductor 156 (e.g., cylindrical conducting sheath).

The dipole antenna 140 includes a proximal portion 142 and a distal portion 144 interconnected by a dielectric spacer at a feed point 146. The distal portion 144 includes a conductive member 145. The distal portion 144 and the proximal portion 142 are of different, unequal lengths so that the dipole antenna 40 is unbalanced. The proximal portion 142 is formed from the inner conductor 150 and the inner insulator 152 which are extended outside the outer conductor 156. In one embodiment, in which the feedline 120 is formed from a coaxial cable, the outer conductor 156 and the inner insulator 152 may be sliced off to reveal the inner conductor 150 as shown in FIG. 18.

The distal portion 144 may be formed from any type of conductive material such as metals (e.g., copper, stainless steel, tin, and various alloys thereof. The portion 144 may have a solid structure and may be formed from solid wire (e.g., 10 AWG) or a cylindrical conductor filled with solder similar to the portion 44 of the assembly 12. The proximal portion 144 is thereafter coupled to the inner conductor 150.

With reference to FIGS. 16-18, the antenna assembly 112 also includes a choke 160. The choke 160 is disposed around the feedline 120 and includes an inner dielectric layer 162 and an outer conductive layer 164. In one embodiment, the choke 160 is a proximally positioned quarter-wave shorted choke that is shorted to the outer conductor 156 of the feedline 120 at the proximal end of the choke 160 by soldering or other means. The dielectric of dielectric layer 162 extends past the choke conductor layer 164 toward the distal end of the assembly 112.

Figure 15:
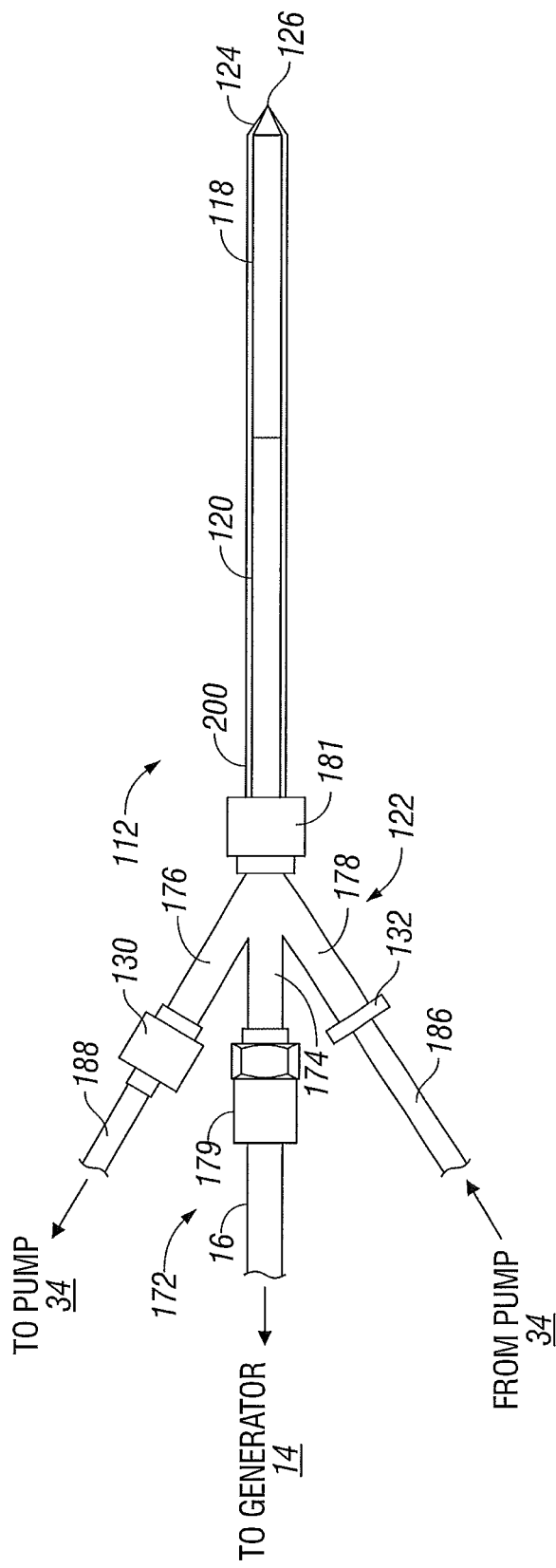
FIG. 15 is a side view of a microwave antenna assembly according to one embodiment of the present disclosure.

The assembly 112 also includes the connection hub 122, as shown in FIG. 15. The connection hub 122 includes a cable connector 179 and the fluid ports 130 and 132. The connection hub 122 may include a three-branch luer type connector 172, with a middle finger 174 being used to house the cable connector 179 and the left and right fingers 176 and 178 to house the outlet and inlet fluid ports 130 and 132, respectively. The cable connector 179 is coupled to the inner conductor 152 and outer conductor 156 that are extended outside the outer conductor 156 at the proximal end of the feedline 120. The connection hub 122 also includes a base 181 disposed at a distal end of the middle finger 174. In one embodiment, the assembly 112 includes one or more inflow tubes 186 which are fed through the right finger 178.

The assembly 112 includes a solid dielectric loading 190 disposed over the dipole antenna 140 replacing the liquid dielectric material of assembly 112. The solid dielectric loading 190 extend from the point of termination of the choke conductor layer 164. More specifically, the assembly 112 includes a fluid seal 192 over the distal end of the choke conductor layer 164. In one embodiment, the loading 190 may be attached to the seal 192 via glue and other means.

The loading 190 may be cylinder-shaped having a central cavity 198 defined therein suitable for insertion over the antenna 140. The loading 190 may also have a tapered end 194 with a pointed tip 196, thereby obviating the need for the tip 48. The loading 190 may also be attached to the distal end of the antenna 140 (e.g., at the distal portion 144 thereof) within the cavity 198. The cavity 198 may have a substantially cylindrical shape suitable to fit over the antenna 140 depending on the cross-sectional shape thereof. In addition, the cavity 198 includes a proximal portion 197 and a distal portion 199 with the proximal portion 197 having a larger inner diameter than the distal portion 199 to accommodate the choke dielectric layer 162. The choke layer 162 may be extended to any length between the choke conductive layer 164 and the feed point 146. To accommodate the extended choke layer 162 the depth of the proximal portion 197 varies accordingly.

The loading 190 has an outer diameter being substantially equal to the thickness of the feedline 120 and the inner diameter being substantially equal to the diameter of the dipole antenna 140. Since the loading 190 is disposed on the dipole antenna 140 and no coolant fluid is going to be in contact therewith, the antenna 140 may not be coated in dielectric shrink wrap to seal its components.

In one embodiment, the dielectric material of the loading 90 may have a dielectric constant of from about 2.5 and 150 and may be made from a ceramic material, such as alumina ceramic or a plastic material, such as a polyamide plastic (e.g., VESPEL® available from DuPont of Wilmington, Del.). The loading 190 acts as a dielectric buffer between the radiating portion 118 and the tissue so that as the electrical properties of the tissue change during ablation the antenna assembly 112 remains halfwave resonant and impedance-matched to the energy delivery system (e.g., the generator 14, the cable 16, etc.) throughout the ablation.

The antenna assembly 112 also includes a coolant jacket 200 disposed between the base 181 and the seal 192. The coolant jacket 200 maybe formed from stainless steel or other suitable medical grade metals. The coolant jacket 200 defines a proximal chamber 201 between the choke conductor layer 164 and the coolant jacket 200 into which a dielectric coolant fluid is supplied through the connection hub 122. More specifically, one or more inflow tube 186 similar to the tubes 86*a* and 86*b* may extend into the chamber 201 to circulate the dielectric coolant fluid through the coolant jacket 200. The seal 192 is disposed between the coolant jacket 200 and the choke conductor layer 164 at the distal ends thereof. The seal 192 may be formed from any type of dielectric (e.g., elastomer) and/or conductive material suitable for sealing the chamber 201 from the loading 190.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. A microwave antenna assembly comprising:
   a feedline including an inner conductor, an outer conductor and an inner insulator disposed therebetween;
   a radiating portion including an unbalanced dipole antenna having a proximal portion and a distal portion of different lengths and a gap therebetween, wherein the proximal portion includes a portion of the inner conductor and the inner insulator and the distal portion includes a conductive member;
   a sleeve disposed around a portion of the outer conductor and the conductive member, the sleeve defining a vacuum chamber therein disposed between a distal end of the outer conductor, a proximal end of the conductive member, and the inner insulator; and
   a choke disposed around a portion of the feedline, the choke including an inner dielectric layer and an outer conductive layer, wherein a distal end of the inner dielectric layer is disposed between a distal end of the outer conductive layer and the gap.

2. The microwave antenna assembly according to claim 1, further comprising:
   a connection hub including a cable connector coupled to the feedline, an inlet fluid port and an outlet fluid port.

3. The microwave antenna assembly according to claim 2, further comprising:
   a seal disposed around a distal end of the outer conductive layer of the choke; and a coolant jacket coupled to the connection hub and the seal thereby defining a proximal chamber around the feedline.

4. The microwave antenna assembly according to claim 3, further comprising:
a solid dielectric loading having central cavity defined therein adapted to fit about the radiating portion, the solid dielectric loading being coupled to the seal.

5. The microwave antenna assembly according to claim 4, wherein the solid dielectric loading is formed from a dielectric material having a dielectric constant from about 2.5 to about 150.

6. The microwave antenna assembly according to claim 3, further comprising:
an inflow tube coupled to the inlet fluid port and disposed within the proximal chamber for supplying a dielectric coolant fluid thereto; and
an outflow tube coupled to the outlet fluid port and in fluid communication with the proximal chamber for withdrawing the dielectric coolant fluid therefrom.

7. The microwave antenna assembly according to claim 2, further comprising:
a tip having an insertion base, a tapered end and a pointed end, wherein the tip is coupled to the distal portion of the unbalanced dipole antenna; and
a sheath coupled to the connection hub and the tip, thereby defining a chamber around the feedline and the radiating portion.

8. The microwave antenna assembly according to claim 2, further comprising:
an inflow tube coupled to the inlet fluid port and disposed within the chamber for supplying a dielectric coolant fluid thereto; and
an outflow tube coupled to the outlet fluid port and in fluid communication with the chamber for withdrawing the dielectric coolant fluid therefrom.

9. The microwave antenna assembly according to claim 1, wherein the outer conductive layer is shorted to the outer conductor of the feedline.

10. The microwave antenna assembly according to claim 1, wherein the inner dielectric layer is selected from the group consisting of a tetrafluorethylene and a perfluorpropylene.

11. A microwave antenna assembly comprising:
a feedline including an inner conductor, an outer conductor and an inner insulator disposed therebetween;
a radiating portion including an unbalanced dipole antenna having a proximal portion and a distal portion of different lengths and a gap therebetween, wherein the proximal portion includes a portion of the inner conductor and the inner insulator and the distal portion includes a conductive member;
a sleeve disposed around a portion of the outer conductor and the conductive member, the sleeve defining a vacuum chamber therein disposed between a distal end of the outer conductor, a proximal end of the conductive member, and the inner insulator; and
a choke disposed around a portion of the feedline, the choke includes an inner dielectric layer and an outer conductive layer, wherein the outer conductive layer is shorted to the outer conductor of the feedline and a distal end of the inner dielectric layer is disposed between a distal end of the outer conductive layer and the gap.

12. The microwave antenna assembly according to claim 11, a sheath disposed over the feedline and the radiating portion defining a chamber around the feedline and the radiating portion, the chamber being adapted to circulate dielectric coolant fluid therethrough.

13. The microwave antenna assembly according to claim 12, further comprising:
a tip having an insertion base, a tapered end and a pointed end, wherein the tip is coupled to the distal portion of the unbalanced dipole antenna.

14. The microwave antenna assembly according to claim 13, wherein the sheath is coupled to the connection hub and the tip.

15. The microwave antenna assembly according to claim 12, wherein the sheath is a polyimide catheter.

16. The microwave antenna assembly according to claim 11, further comprising:
a connection hub including a cable connector coupled to the feedline, an inlet fluid port and an outlet fluid port.

17. The microwave antenna assembly according to claim 11, further comprising:
an inflow tube coupled to the inlet fluid port and disposed within the chamber for supplying the dielectric coolant fluid thereto; and
an outflow tube coupled to the outlet fluid port and in fluid communication with the chamber for withdrawing the dielectric coolant fluid therefrom.

18. A microwave antenna assembly comprising:
a feedline including an inner conductor, an outer conductor and an inner insulator disposed therebetween;
a radiating portion including an unbalanced dipole antenna having a proximal portion and a distal portion that are of different lengths and a gap therebetween, wherein the proximal portion includes a portion of the inner conductor and the inner insulator and the distal portion includes a conductive member;
a sleeve disposed around a portion of the outer conductor and the conductive member, the sleeve defining a vacuum chamber therein disposed between a distal end of the outer conductor, a proximal end of the conductive member, and the inner insulator;
a choke disposed around a portion of the feedline, the choke includes an inner dielectric layer and an outer conductive layer, wherein the outer conductive layer is shorted to the outer conductor of the feedline and the inner dielectric layer extends past the outer conductive layer, wherein a distal end of the inner dielectric layer is disposed between a distal end of the outer conductive layer and the gap;
a coolant jacket disposed over the feedline defining a proximal chamber around the feedline, the chamber being adapted to circulate dielectric coolant fluid therethrough; and
a solid dielectric loading having central cavity defined therein adapted to fit about the radiating portion, the solid dielectric loading extending from the coolant jacket.

19. The microwave antenna assembly according to claim 18, further comprising:
a connection hub including cable connector coupled to the feedline, an inlet fluid port and an outlet fluid port; and
a seal disposed around a distal end of the outer conductive layer of the choke, wherein the coolant jacket is coupled to the connection hub and the seal thereby defining a proximal chamber around the feedline.

20. The microwave antenna assembly according to claim 18, wherein the solid dielectric loading is formed from a dielectric material selected from the group consisting of an alumina ceramic or a polyamide plastic and having a dielectric constant from about 2.5 to about 150.

21. The microwave antenna assembly according to claim 18, further comprising:
   an inflow tube coupled to the inlet fluid port and disposed within the proximal chamber for supplying a dielectric coolant fluid thereto; and
   an outflow tube coupled to the outlet fluid port and in fluid communication with the proximal chamber for withdrawing the dielectric coolant fluid therefrom.

22. The microwave antenna assembly according to claim 18, wherein the coolant jacket is formed from a medical grade metal.

* * * * *